United States Patent [19]

Dory

[11] 4,274,421

[45] Jun. 23, 1981

[54] ECHO SOUND APPARATUS INCLUDING AN OSCILLATING MIRROR FOR USE IN MEDICAL DIAGNOSIS

[75] Inventor: Jacques Dory, Meaux, France

[73] Assignee: C. G. R. Ultra Sonic, France

[21] Appl. No.: 956,706

[22] Filed: Nov. 1, 1978

[30] Foreign Application Priority Data

Nov. 23, 1977 [FR] France ................. 77 35201

[51] Int. Cl.$^3$ .................................................. A61B 5/02
[52] U.S. Cl. ........................................ 128/660; 73/620
[58] Field of Search ............................. 128/660–661; 73/618–621, 611

[56] References Cited

U.S. PATENT DOCUMENTS

| 3,996,792 | 12/1976 | Kubota et al. | 73/611 |
| 4,084,582 | 4/1978 | Nigam | 73/620 |
| 4,092,867 | 6/1978 | Matzuk | 73/619 |
| 4,106,492 | 8/1978 | Schuette et al. | 128/661 |
| 4,110,723 | 8/1978 | Hetz et al. | 73/620 |
| 4,120,291 | 10/1978 | Paton et al. | 73/618 |
| 4,137,775 | 2/1979 | Le May | 73/620 |
| 4,137,777 | 2/1979 | Haverl et al. | 128/660 |
| 4,151,834 | 5/1979 | Sato et al. | 128/660 |

FOREIGN PATENT DOCUMENTS 2710038  7/1978  Fed. Rep. of Germany ........... 128/660

OTHER PUBLICATIONS

Holasek, E. et al., "Direct Contact Hand-held Diagnostic B-Scanner".

Primary Examiner—Robert W. Michell
Assistant Examiner—Francis J. Jaworski
Attorney, Agent, or Firm—William A. Drucker

[57] ABSTRACT

An echo sounding apparatus which includes an ultrasonic transmitter-receiver probe 3 generating a horizontal ultrasonic beam and a mirror 4 inclined at 45° with respect to the said beam and driven by a torque motor 5 for oscillatory conical motion about an axis which coincides with the said beam. A housing 1 containing a coupling liquid transmits the investigation ultrasonic beam reflected on the mirror through a transparent membrane 2. An auxiliary ultrasonic reflector, which follows the angular displacement of the mirror, cooperates with an auxiliary transducer, operated in synchronization with the said probe, for providing a signal indicative of the angular position of the mirror. The torque motor is controlled from the said signal so that the mirror is oscillated in accordance with a pre-determined scanning law and a circuit controls the displacement of the beam of a cathode ray tube so as to provide a type B display where the scanning of the screen of this tube continuously corresponds to the displacement of the ultrasonic beam.

5 Claims, 3 Drawing Figures

ECHO SOUND APPARATUS INCLUDING AN OSCILLATING MIRROR FOR USE IN MEDICAL DIAGNOSIS

BACKGROUND OF THE INVENTION

The invention relates to the technique of sounding biological tissue with ultrasonic pulses and the visual presentation of the resulting echo signals on the screen of a cathode ray tube in the form of what is known as a type B display.

With this type of display the scanning of the screen of the cathode ray tube corresponds continuously to the displacement of the ultrasonic beam in the medium being examined, the beam being swept through a plane.

THE PRIOR ART

With known echo sounding apparatus, employing a type B display, the ultrasonic transmitting probe is usually displaced over the surface of the patient's body by hand and with this technique it is impossible to effect a dynamic analysis, i.e. it is impossible to obtain a display with the organs of the patient's body in motion. The use of a probe made up of a number of transducer elements with a high rate of switching between such elements has been proposed in order to be able to effect a dynamic analysis. This results in complicated equipment which cannot be widely used because of the high cost.

OBJECT OF THE INVENTION

The invention would facilitate the construction of very simple apparatus of reduced size would be particulary useful in examining small organs of the body (e.g. the eye or the thyroid gland) where a penetration of only a few centimeters is involved or of organs where a deeper penetration is required (e.g. up to 20 cm) but only within a limited angular sector (e.g. cardiologic and obstetric examinations).

SUMMARY OF THE INVENTION

The present invention is utilized in an apparatus comprising an ultrasonic pulse transmitting-receiving probe used in conjunction with a plane moving mirror and a liquid contained in a housing which serves to couple the apparatus with the medium being examined through a transparent membrane forming the base of the housing; a cathode ray tube and an electronic control circuit which ensures that the scanning of the screen of that tube by the electron writing beam continuously corresponds to the displacement of the ultrasonic beam in the medium being examined. In accordance with the invention, the said mirror is inclined at 45° with respect to the ultrasonic beam transmitted by the probe and is driven for oscillatory conical motion about an axis which coincides with the said beam. The probe is mounted in the side wall of the said housing and has a transmitting-emitting surface opposite the mirror within the housing; an electric motor, having no rotating contacts, drives a spindle which supports the mirror and is controlled by an electronic circuit associated with means, immersed in the housing and having no contact with the mirror, for providing an electrical signal corresponding to the angular position of the mirror.

In a preferred embodiment of the apparatus, the said means of providing a signal corresponding to the angular position of the mirror consist of an auxiliary transducer, operated in synchronism with the probe and cooperating with an auxiliary ultrasonic reflector which follows the angular displacement of the mirror, means for providing a constant-slope saw-tooth voltage, the rise in voltage for each cycle being interrupted by the echo signals picked up by the auxiliary transducer and means for detecting the peak voltage amplitude of the saw-tooth voltage.

Other features as well as the advantages of the invention will become evident on referring to the following description.

DESCRIPTION OF THE PREFERRED EMBODIMENT

Figure 2:
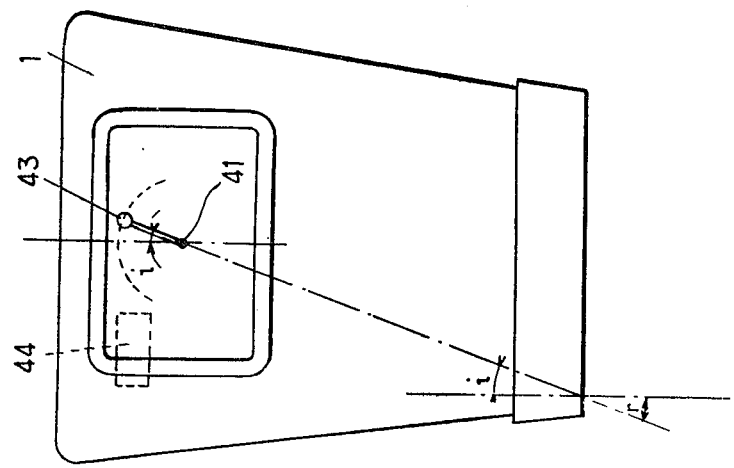
FIG. 2 is an end view of this sounding head.
Figure 1:
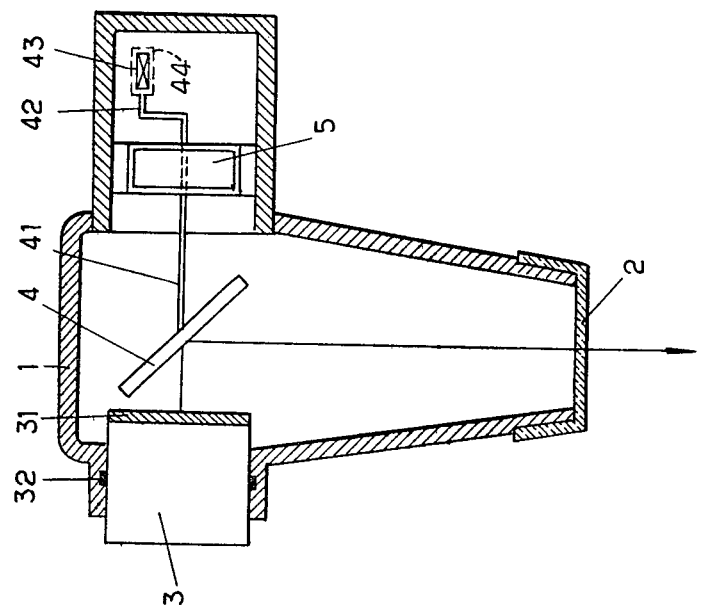
FIG. 1 is a longitudinal cross section of the sounding head of the apparatus according to the invention.

FIGS. 1 and 2 illustrate a housing 1 in the form, for example, of a parallel sided box surmounting a truncated pyramid extension with a projection to one side housing a motor, as described below.

The side walls of the housing are made of material that is opaque to ultrasonic radiation and preferably covered with a substance that will absorb ultrasonic signals. The base 2 of the housing consists of a membrane that is transparent to ultrasonic radiation and preferably made from material having substantially the same acoustic impedance as organic tissue and intended to be applied to the skin of the patient.

A piezo-electric transducer 3 is mounted in the wall of the housing, the transmitting-emitting surface 31 being vertical and operating in conjunction with a plane mirror 4 inclined at 45° with respect to the horizontal ultrasonic beam transmitted by transducer 3. The mirror 4 consists, for example, of a metal plate. The seal 32 ensures that the housing remains water-tight.

The mirror 4 is displaced in an oscillatory manner by means of the horizontally mounted spindle 41 which coincides with the horizontal beam such that the projected ultrasonic beam sweeps through an angle lying in the vertical plane of symmetry of the housing perpendicular to the plane of FIG. 1 and parallel to that of FIG. 2.

The spindle 41 is directly attached to the electric motor 5 immersed in the liquid contained in the housing 1. This motor which is accommodated in the housing projection mentioned above is of a type having no rotating contacts and is preferably a torque motor. Thus the arrangement constitutes a light-weight, one-piece, oscillating assembly with no rotating joints (source of leaks and unwanted friction) which is easy to construct and which can be very reliable in operation.

Figure 3:
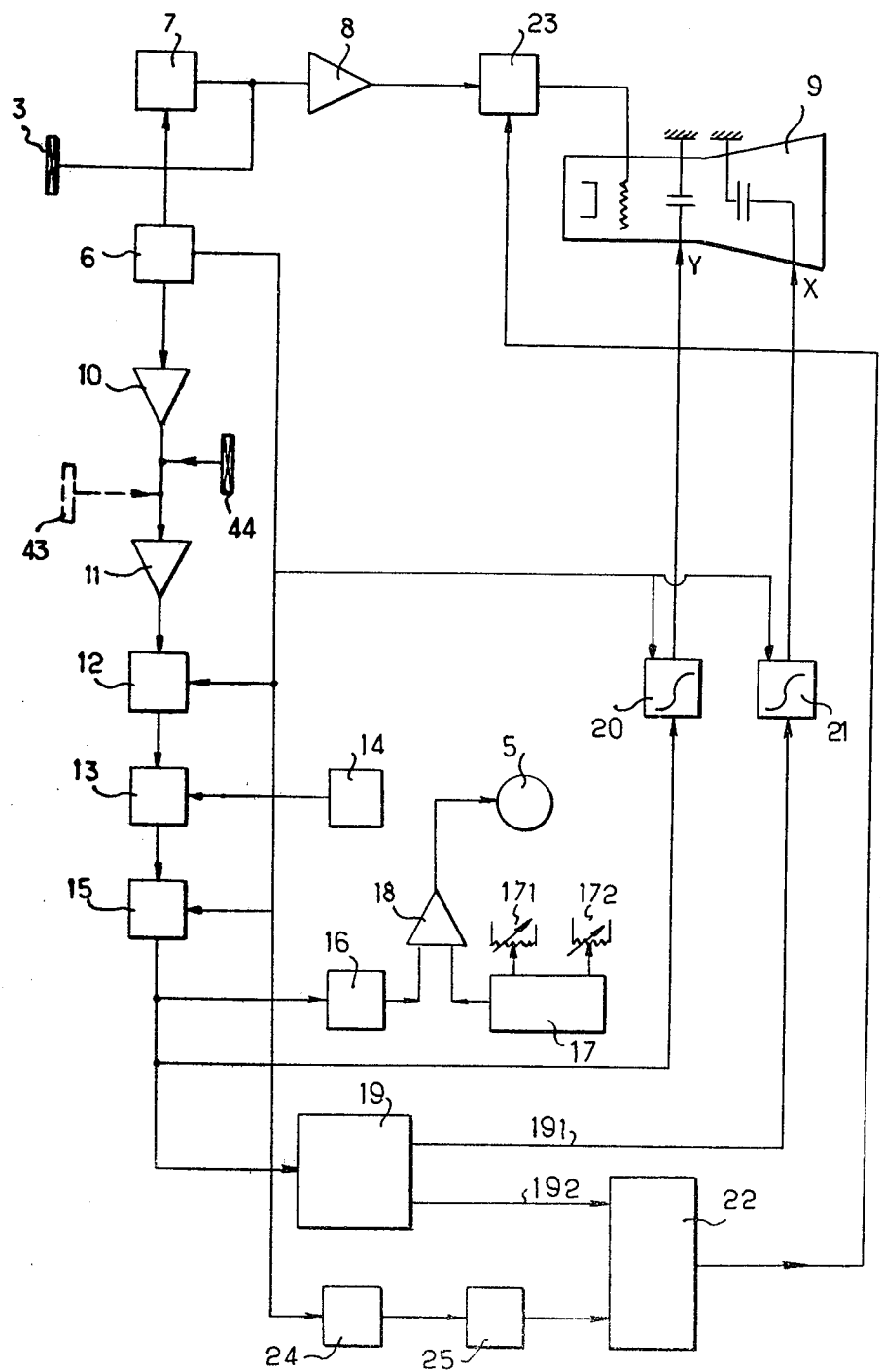
FIG. 3 is a schematic representation of the electronic circuits of the apparatus.

FIG. 3 illustrates the general arrangement of a repetitive electrical pulse generator 6 which modulates the high frequency transmitter 7, the resulting signal operating the transducer 3 in the usual way. The echo pulses go to the receiver 8 whose output serves as a modulating signal going to the control electrode of the cathode ray tube 9.

Coming back to FIGS. 1 and 2, it appears that rotation of the spindle 41 results in a corresponding displacement of the parallel spindle extension 42 which carries an auxiliary reflector 43 illustrated as a cylindrical mirror. An auxiliary transducer 44 attached to the vertical wall of the motor housing projection, transmits, in a direction at right angles with the plane of FIG. 1, an additional horizontal ultrasonic beam towards the reflector 43. The period of time separating a transmitted pulse from the reception of a corresponding echo signal is proportional to sin i plus a constant (FIG. 2).

The auxiliary transducer 44 is driven by the signals from the pulse generator 6 and associated amplifier 10. The echo signals picked up from the auxiliary reflector 43 are amplified by the amplifier 11 and fed to the flip-flop 12. The reset to zero input of this flip-flop is connected to the pulse generator 6. Thus, the flip-flop provides a square wave output, the front of any square wave corresponding to the time of transmission of an ultrasonic pulse and the rear of that square wave to the time of reception of the corresponding echo from the auxiliary mirror. The width of a square wave at any instant of time is proportional to sin i plus a constant where i is the angle that the mirror makes with the reference vertical at that instant of time.

The square wave signals go to the gate 13 which is also supplied with clock pulses from the clock pulse generator 14. The clock pulses are thus transmitted to the counter 15 for the duration of each square wave such that the counter output provides digital values of sin i. A digital to analogue convertor 16 converts the digital signals to analogue voltages which serve as feedback signals for the operation of the motor and the displacement of the electron beam of the cathode ray tube as explained below.

The generator 17 provides a saw tooth voltage output whose frequency can be adjusted, for example, to be between 5 and 10 Hz. The generator 17 is arranged so that the amplitude and d.c. level of the saw-tooth signal can be adjusted in response to the setting of the potentiometers 171 and 172 respectively. This saw-tooth signal goes to one input of the differential amplifier 18, the other input being supplied with the analogue voltage from the digital to analogue converter 16. The output of the differential amplifier 18 is applied to the motor 5 as a demand for that motor to rotate. This type of servo control, a well known technique in itself, continuously determines the angular position of the mirror. Thus the frequency of oscillation of the mirror can be varied from 5 to 10 Hz while the amplitude of the saw-tooth signal from the generator 17 will determine the angle of sweep of the ultrasonic beam and the d.c. level of the same signal, the orientation of the axis of the said beam in the scanning plane.

The cathode ray tube scanning control circuit includes a programmable read only store 19 connected to the counter 15 and arranged to supply the signals cos i and 1/cos i at the outputs 191 and 192 respectively.

The digital sin i and cos i signals go via the integrators 20 and 21 respectively to the Y and X plates of the cathode ray tube 9. These integrators supply output voltages of the form $C_1 t \sin i$ and $C_1 t \cos i$ respectively such that the scanning of the cathode ray tube screen continuously corresponds to the displacement of the ultrasonic beam in the coupling liquid contained in the housing of the apparatus and in the medium being examined. This is on the assumption, of course, that there is no appreciable refraction of the ultrasonic beam in going from one medium to another which is the case when water is employed as the coupling liquid, the speed of propagation then being the same in both media.

The output 192 from the store 19 goes to the comparator 22 while the other input of this latter is supplied with a signal from the counter 25 which is in turn driven by clock pulses from the clock pulse generator 24. The output of this comparator operates the gate 23 which allows the echo signal from the receiver 8 to go the control electrode of the cathode ray tube 9.

Thus for each transmission cycle the gate 23 is only opened when the number of pulses delivered from the clock pulse generator 24, this latter being triggered by a transmission signal from the pulse generator 6, is equal to the digital value of 1/cos i. The clock pulse period is set to the value d/c, where d is the distance that an emitted ultrasonic signal must travel in arriving at the membrane when the beam is at right angles to that membrane. Thus the gate is opened at the end of a period of time of d/c. cos i, i.e. at the instant when the ultrasonic pulse effectively reaches the membrane. Thus the display of any parasitic echo signals resulting from reflections within the housing are suppressed. The circuit can also be set up so that the signal from the comparator results in a display of the membrane on the screen of the cathode ray tube.

It will be understood that modifications of the servo control of the motor and of the scanning of the cathode ray tube screen could be imagined and designed by those skilled in the art, without however departing from the basic concept of the invention. Nevertheless the digital scanning control system that has been described is particularly simple and attractive and is regarded as a preferred embodiment.

The proposed system for detecting the position of the mirror, based on the use of an auxiliary transducer and a reflector, is also a particularly attractive arrangement.

In the case of applications such as obstetrics, where the apparatus is used to examine locations close to the membrane, it is necessary for the sector swept out by the ultrasonic beam to have a trapezoidal shape and in this case the distance d cannot be small. Thus for such applications it is required that the distance travelled by the ultrasonic pulse within the housing of the apparatus should be at least equal to that covered in the medium being examined, for example that d should be not less than 20 cm. Given this arrangement, the second echo reflected from the membrane will appear after reception of the useful signal resulting from the reflection from within the medium concerned so that there will be no interference in conducting the examination. Since it has been observed that the scattering of the ultrasonic radiation from the side walls of the housing can result in a small proportion of the ultrasonic waves returning to the mirror via inverse paths as a result of successive reflections from the membrane and the said side walls it is clearly an advantage if the said walls can be covered with an absorbent material.

Cardiology, as opposed to obstetrics, requires that the sector swept out by the ultrasonic beam has a triangular shape so as to facilitate the penetration of the beam between adjacent ribs and in this case it is preferable to locate the membrane within a few centimeters from the surface of the mirror from which the ultrasonic waves are reflected. With this arrangement, the echo signals due to successive reflections from the membrane can be superimposed on the useful signal and it is therefore necessary to reduce the amplitude of the unwanted sound waves.

Experience shows that this reduction can be achieved by employing a coupling liquid that absorbs ultrasonic radiation and on using a membrane having an acoustic impedance very close to that of the two media.

In practice the coupling liquid can consist of water with a cellulose compound additive which results in an appreciable increase in the coefficient of absorbtion without having much effect either on the acoustic impedance or the speed of propagation of the ultrasonic radiation. The membrane can be made from a polyethylene or a polyurethane.

These treatments result in an appreciable increase in the signal/noise ratio without resulting in any excessive reduction in the sensitivity of the apparatus (providing that a suitable coefficient of absorption is determined). The invention also makes it possible to construct very compact apparatus (e.g. with a housing 3 to 4 cm deep). The angle of examination is reduced. This is particularly useful for ophthalmic work and for the examination of the thyroid gland and other organs that are near to the surface.

I claim:

1. An echo sounding apparatus comprising: a fluid-tight housing having side walls and a bottom wall, at least part of the surface of said bottom wall being transparent to ultrasonic waves; a transmitting-receiving ultrasonic probe fixedly mounted in a surface portion of said side-walls and having a transmitting-receiving surface within said housing substantially at right angles with the bottom wall; a liquid contained in the housing and adapted to transmit the ultrasonic waves from the probe to the bottom wall; an electric motor, of a type having no rotating contacts, fixedly mounted within the housing, and immersed in the said liquid; a spindle, supported and rotated by the said motor, along an axis at right angles with the said transmitting-receiving surface; a plane mirror, rotatably mounted about said spindle within said housing and facing said transmitting-receiving surface, said mirror being inclined at 45° with respect to said spindle; control means for controlling the said motor so as to generate an oscillatory conical motion of the mirror about the said axis, said control means comprising means, immersed in the liquid and having no contact with the mirror, for providing an electrical signal corresponding to the angular position of the mirror; pulse transmitter-receiver circuit means connected to the said probe and display means, coupled to the transmitter-receiver circuit means.

2. An apparatus according to claim 1, wherein said means for providing a signal corresponding to the angular position of the mirror consists of an auxiliary ultrasonic reflector rigidly attached to the said spindle, a fixed auxiliary transducer and means coupled to the said auxiliary transducer, transmitting and receiving auxiliary ultrasonic pulses, in synchronism with the said pulse transmitter-receiver circuit means, and means for determining the time of propagation of the said auxiliary pulses from the said auxiliary transducer to the said auxiliary reflector.

3. An apparatus, according to claim 1, wherein the said control means includes a reference saw-tooth generator with means for adjusting the frequency, the amplitude and the d.c. level of its output saw-tooth voltage, and means for comparing the said output saw-tooth voltage to the said electrical signal.

4. An apparatus according to claim 1, wherein said display means comprises: a cathode ray tube having horizontal and vertical deflection elements and a brightness control electrode; an electronic scanning control circuit including means, connected to the said means for providing an electrical signal, for producing digital signals proportional to the sine and cosine of the angle defining the position of the mirror; integrators of these digital values, which are connected respectively, to the said vertical and horizontal deflection elements; further means, connected to the means for producing digital signals, for producing an additional digital signal inversely proportional to the cosine of said angle; comparator means having a first input connected to the said further means for receiving the said additional signal and a second input; clock pulse generator means for generating trains of auxiliary pulses which are respectively released with the respective transmission pulses, said auxiliary pulses having a period proportional to the ratio of the distance between the mirror and the membrane and the speed of propagation of the ultrasonic waves in the coupling liquid, said clock pulse generator means being connected to the said second input; said comparator means having an output; gate means connecting the said transmitter-receiver circuit means to the said brightness control electrode, said gate means having a control input which is connected to the output of the comparator means.

5. An apparatus, according to claim 1, wherein the said liquid has a pre-determined absorption power with respect to ultrasonic waves, while having substantially the same acoustic impedance as the investigated medium.

* * * * *